United States Patent [19]

Cochran

[11] Patent Number: 5,143,064
[45] Date of Patent: Sep. 1, 1992

[54] MEDICAL CHILLING APPARATUS

[76] Inventor: William P. Cochran, 300 Royal Oaks Blvd. #1303, Franklin, Tenn. 37064

[21] Appl. No.: 610,160

[22] Filed: Nov. 5, 1990

[51] Int. Cl.$^5$ ................................................ A61F 7/00
[52] U.S. Cl. .................................... 128/402; 128/382
[58] Field of Search ............. 128/400, 402, 403, 82.1, 128/24.1, 382; 62/530

[56] References Cited

U.S. PATENT DOCUMENTS

| | | | |
|---|---|---|---|
| 2,702,552 | 2/1955 | Moodie | 128/402 |
| 2,832,336 | 4/1958 | Davis et al. | 128/402 |
| 4,071,031 | 1/1978 | Lowman | 128/402 |
| 4,329,997 | 5/1982 | de Yampert et al. | 128/402 |

Primary Examiner—Edward M. Coven
Assistant Examiner—Mark S. Graham
Attorney, Agent, or Firm—Leon Gilden

[57] ABSTRACT

An apparatus is set forth to effect selective chilling of an extremity of an individual's appendage, such as the ankle and foot portion, wherein the apparatus includes a container with a cylindrical opening directed through an end wall thereof, with the opening including a clamping collar. The clamping collar includes an "L" shaped bag member mounted thereabout, with a clamp securing the bag member to the clamping collar, and the bag member including an opening aligned with the cylindrical opening. A support is positioned underlying the bag member, with the container defining a cavity about the bag member to accept a chilling medium such as fluid and ice mixture.

1 Claim, 4 Drawing Sheets

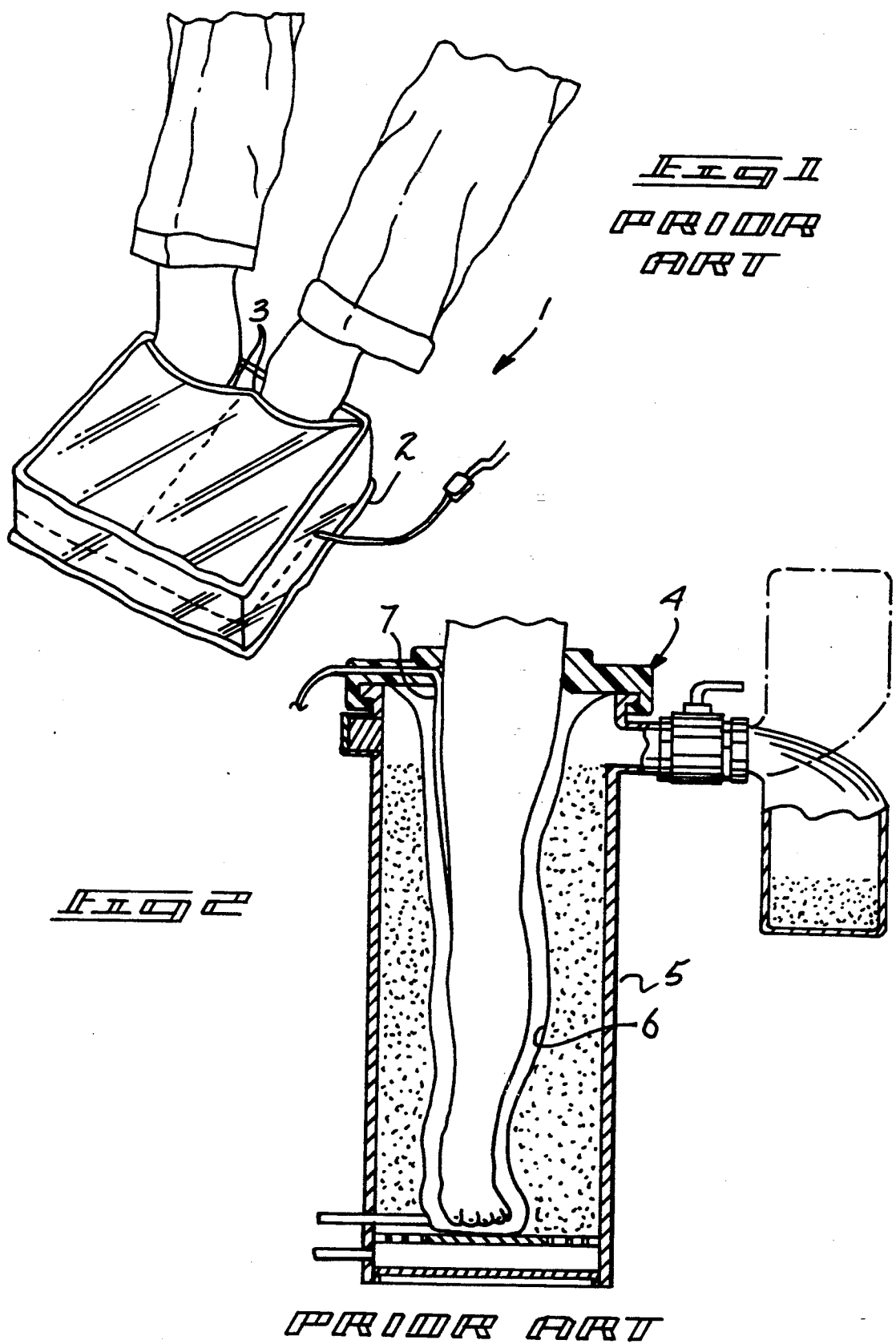

MEDICAL CHILLING APPARATUS

BACKGROUND OF THE INVENTION

1. Field of the Invention

The field of invention relates to medical chilling devices, and more particularly pertains to a new and improved medical chilling apparatus wherein the same provides for selective chilling of an outer extremity of an individual's leg portion.

2. Description of the Prior Art

The medical field has utilized various apparatus to effect application of a variant temperature to an individual's body portion to enhance healing. Such apparatus in exemplified in U.S. Pat. No. 4,513,736 to Thurber wherein a massaging device includes a heating pad underlying the massaging device.

U.S. Pat. No. 4,648,392 to Cartier provides an apparatus for effecting the directing of pressure in a surrounding relationship relative to a leg portion of an individual.

U.S. Pat. No. 4,005,531 to Weintreub, et al. provides a cooler appartus wherein a foot portion is positioned upon a support to effect a temperature reduction of an individual's foot member.

U.S. Pat. No. 4,586,505 to Nagle sets forth an elastomeric band mounting a heating or cooling pad for application to an individual's body part.

U.S. Pat. No. 4,688,572 to Hubbard, et al. sets forth a thermal pack wherein a band member includes a pocket for receiving a medium to heat an individual's body portion.

As such, it may be appreciated that there continues to be a need or a new and improved medical chilling apparatus as set forth by the instant invention which addres both the problems of ease of use as well as effectiveness in construction and in this respect, the present invention substantially fulfills this need.

SUMMARY OF THE INVENTION

In view of the foregoing disadvantages inherent in the known types of medical chilling devices now present in the prior art, the present invention provides a medical chilling apparatus wherein the same provides for appllication of a cooling medium directed through an impermeable membrane of an individual's foot portion from the chilling medium. As such, the general purpose of the present invention, which will be described subsequently in greater detail, is to provide a new and improved medical chilling apparatus which has all the advantages of the prior art chilling apparatus and none of the disadvantages.

To attain this, the present invention provides an apparatus setting forth selective chilling of an extremity of an individual's appendage, such as the ankle and foot portion, wherein the apparatus includes a container with a cylindrical opening directed through as end well thereof, with the opening including a clamping collar. The clamping collar includes an "L" shaped bag member mounted thereabout, with a clamp securing the bag member to the clamping collar, and the bag member including an opening aligned with the cylindrical opening. A support is positioned underlying the bag member, with the container defining a cavity about the bag member to accept a chilling medium such as fluid and ice mixture.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Pat. and Trademark office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved medical chilling apparatus which has all the advantages of the prior art chilling apparatus and none of the disadvantages.

It is another object of the present invention to provide a new and improved medical chilling apparatus which may be easily and efficiently manufactured and marketed.

It is a further object of the present invention to provide a new and improved medical chilling apparatus which is of a durable and reliable construction.

An even further object of the present invention is to provide a new and improved medical chilling apparatus which is susceptible of a low cost of manufacture with regard to both materials and labor, and which accordingly is then susceptible of low prices of sale to the consuming public, thereby making such medical chilling apparatus economically available to the buying public.

Still yet another object of the present invention is to provide a new and improved medical chilling apparatus which provides in the apparatuses and methods of the prior art some of the advantages thereof, while simultaneously overcoming some of the disadvantages normally associated therewith.

Still another object of the present invention is to provide a new and improved medical chilling apparatus wherein the same is arranged for anatomically accepting an individual's foot member therewithin to permit application of a chilling medium through the membrane.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a prior art medical heating device.

FIG. 2 is an orthographic cross-sectional illustration of a prior art apparatus to introduce pressure to an individual's leg portion.

DESCRIPTION OF THE PREFERRED EMBODIMENT

Figure 3:
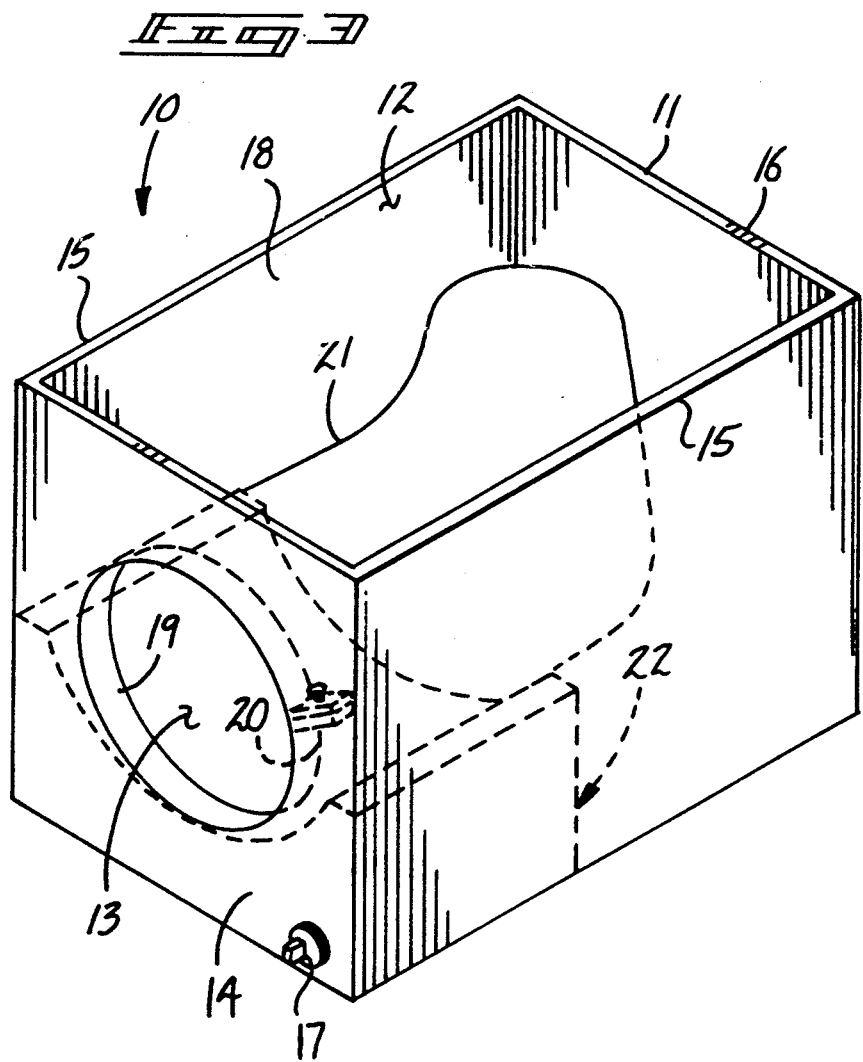
FIG. 3 is an isometric illustration of the instant invention.
Figure 4:
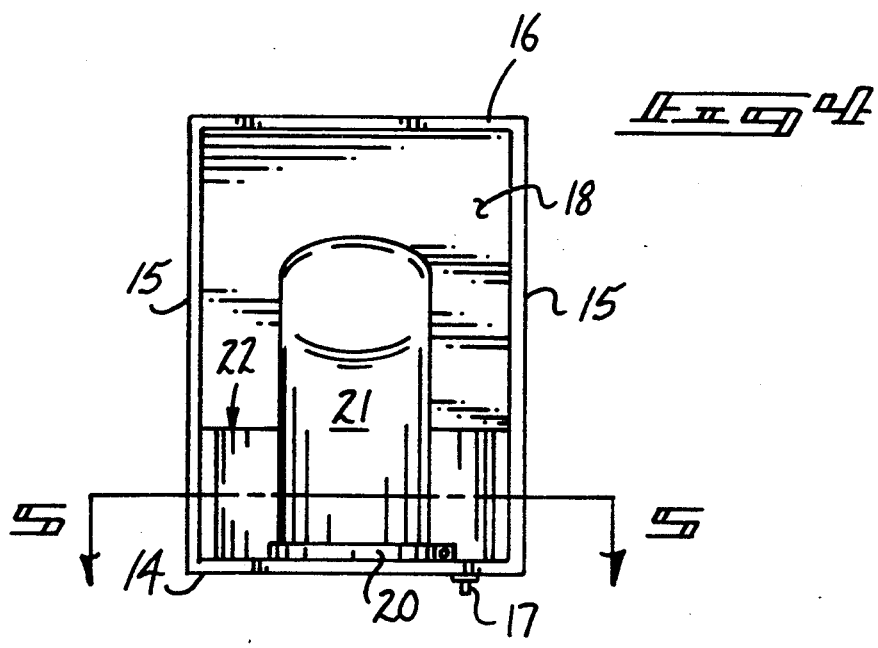
FIG. 4 is an orthographic top view of the instant invention.
Figure 5:
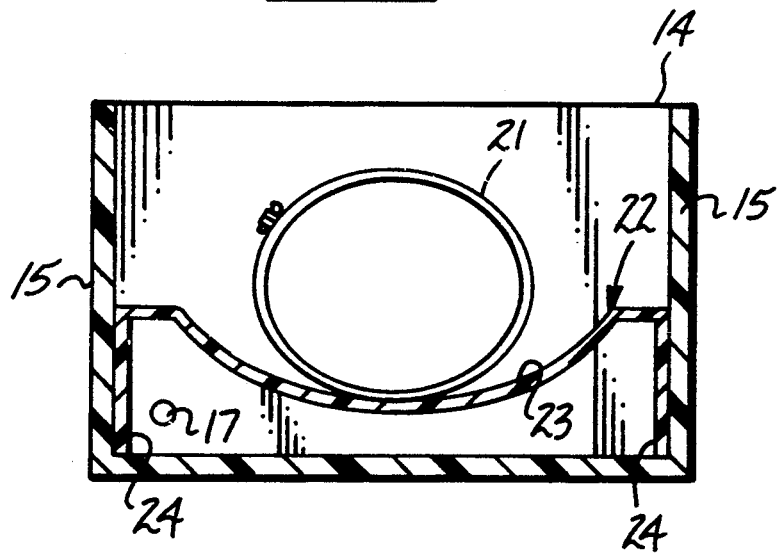
FIG. 5 is an orthographic view, taken along the lines 5—5 of FIG. 4 is the direction indicated by the arrows.
Figure 6:
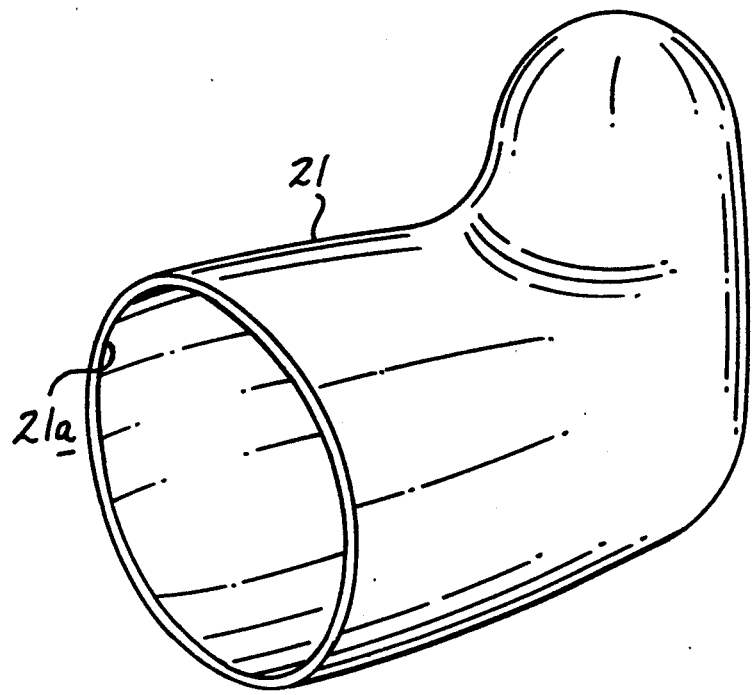
FIG. 6 is an isometric illustration of the "L" shaped bag member utilized by the instant invention defining an impermeable membrane.
Figure 7:
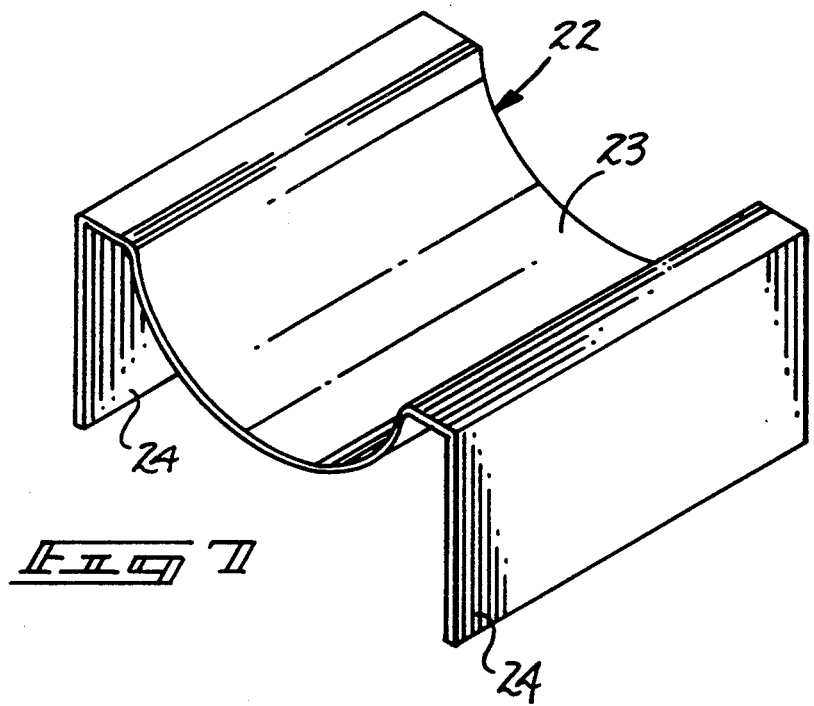
FIG. 7 is an isometric illustration of the support utilized by the instant invention.
Figure 8:
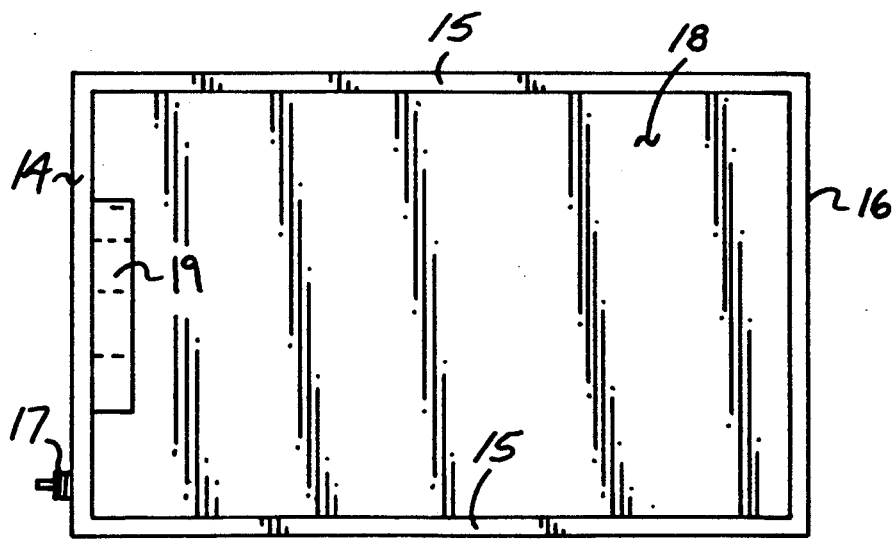
FIG. 8 is a top orthographic view of the instant invention with the support and bag member removed therefrom.

With reference now to the drawings, and in particular to FIGS. 1 to 8 thereof, a new and improved medical chilling apparatus embodying the principles and concepts of the present invention and generally designated by the reference numeral 10 will be described.

FIG. 1 illustrates a prior art heat application apparatus 1, wherein pockets 3 overlie a heating pad 2 to enhance medical treatment of an individual's foot members as set forth in U.S. Pat. No. 4,513,736. FIG. 2 illustrates a further prior art medical treatment organization 4, wherein a container 5 includes an outer bag 6 separated from an inner bag 7 to define a cavity therebetween receiving mercury fluid therebetween, with a granular mixture arranged between the outer bag 6 and the container 5 to receive a granular mixture for application of pressure about an individual's leg portion, as set forth in U.S. Pat. No. 4,648,392.

More specifically, the medical chilling apparatus 10 of the instant invention essentially comprises a box shaped housing 11, including an open upper end 12, with a front wall 14 including a cylindrical opening 13 directed medially therethrough. The front wall 14 is spaced from an end wall 16 with spaced side walls 15 included defining a container overlying the floor thereof. The front wall 14 further includes a removable drain plug 17 mounted adjacent the floor of the container to permit draining of fluid subsequent to use of the organization and to further permit monitoring of fluid contained within the container cavity 18 defined within the container and to maintain a proper ice/fluid mixture therewithin. The cylindrical opening 13 includes a cylindrical clamping collar 19 coextensive with the cylindrical opening 13 and directed interiorly of the container cavity 18. An "L" shaped fluid impermeable bag 21 defining an impermeable membrane includes a cylindrical forward end 21a, with a bag diameter substantially equal to a collar diameter defined by the cylindrical collar 19. A cylindrical clamp 20 is provided to surroundingly engage the forward end 21a and the cylindrical collar 19 to secure the "L" shaped bag 21 within the cavity 18. A support 22 is provided to include an arcuate top portion 23. The arcuate top portion 23 is in alignment with the cylindrical opening 13. A predetermined width is defined between the side walls 15, wherein the support 22 is defined by a support width substantially equal to the predetermined width, and wherein the support defines a support length less than a predetermined length defined between the end wall 16 and the front wall 14.

To treat an individual's ankle and foot portion, the same is inserted within the bag member 21 that in turn is clamped to the cylindricla collar 19, as noted above. An ice/fluid mixture is positioned within the cavity 18 to permit application of a cooling and chilling medium to the ankle and foot portion of the individual that is directed within the bag 21. Further it should be noted that the container may be elevated as desired to position an individual's ankle and foot portion as required for treatment.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form , function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be restored to, falling within the scope of the invention.

What is claimed as being new and desired to be protected by Letters Patent of the United States is as follows:

1. A medical chilling apparatus comprising,
    a housing, the housing including a floor, a front wall, an end wall and spaced parallel side walls, and
    a cylindrical opening directed medially through the front wall, and
    a membrane means mounted interiorly of the housing and secured to the cylindrical opening for securement of an individual's foot therewithin, and
    a chilling medium positioned within the housing in contiguous relationship with the membrane means for directing chilling of an anatomical body portion positioned within the membrane means, and
    wherein the membrane means defines an "L" shaped fluid impermeable bag member, the bag member including a cylindrical forward end defining a bag diameter, and the cylindrical opening including a cylindrical collar defining a collar diameter, wherein the collar diameter is equal to the bag diameter, and a cylindrical clamp removably mounted about the cylindrical forward end of the bag member, and wherein the front wall includes a drain plug removably mounted through the front wall adjacent the floor of the housing, and wherein the bag member is wholly contained within the housing, and the housing includes an open upper end for reception of a chilling medium within the housing, and wherein the housing further includes a support, the support includes an arcuate top portion, wherein the arcuate top portion is in tangential alignment with a lower end portion of the cylindrical opening to receive and position the bag member thereon, and the support includes spaced parallel side legs, the spaced parallel side legs defining a predetermined width, and a width defined between the side walls interiorly of the housing equals the predetermined width, and the support is defined by a support length, and a length defined between the front wall and the end wall interiorly of the housing defines a predetermined length, wherein the predetermined length is greater than the support length.

* * * * *